United States Patent [19]

Green et al.

[11] 4,305,296
[45] Dec. 15, 1981

[54] ULTRASONIC IMAGING METHOD AND APPARATUS WITH ELECTRONIC BEAM FOCUSING AND SCANNING

[75] Inventors: Philip S. Green; Dilip G. Saraf, both of Atherton; James F. Havlice, Los Altos, all of Calif.

[73] Assignee: SRI International, Menlo Park, Calif.

[21] Appl. No.: 119,937

[22] Filed: Feb. 8, 1980

[51] Int. Cl.³ .......................................... G01N 29/04
[52] U.S. Cl. .................................................. 73/626
[58] Field of Search ........................ 73/626, 628, 633; 367/103, 138; 128/660

[56] References Cited

U.S. PATENT DOCUMENTS

| | | | |
|---|---|---|---|
| 3,936,791 | 2/1976 | Kossoff | 73/626 |
| 4,161,122 | 7/1979 | Buchner | 73/626 |
| 4,164,213 | 8/1979 | Hölzler | 73/626 |
| 4,241,610 | 12/1980 | Anderson | 73/626 |

*Primary Examiner*—Anthony V. Ciarlante
*Attorney, Agent, or Firm*—Victor R. Beckman

[57] ABSTRACT

Method and apparatus for pulsed ultrasonic imaging of a section of the interior of an object from reflections by internal discontinuities of recurrent transmitted pulses of ultrasonic energy, are provided. There is included a transducer array comprising a plurality of adjacent transducer elements for converting echo signals received from discontinuities within the object to equivalent electrical signals. Range gated signal processing means are provided for processing electrical signals from the transducer array reflected from discontinuities within any one of a plurality of range zones within the section to be imaged to provided range gated signals representative of segments of lines within the section to be imaged. The signal processing means includes electronic receiver beam focusing and scanning means for focusing the transducer array at the range zone at which the signals are range gated and for scanning the same. Visual display means for visual display of the line segment signals are provided for visual display of the entire section to be imaged. The signal processing means may include digital scan converter means for temporary storage of received signals for display thereof at a conventional TV monitor. Different numbers of transducer elements are employed for beam forming at the different range zones; a maximum number of adjacent transducer elements being used for operation at the zone farthest from the transducer array, and decreasing numbers being used for zones nearer the array. The electronic beam focusing means includes a plurality of fixed delay means, at least some of which are employed for focusing at a plurality of range zones thereby minimizing the total number required for operation of the system.

28 Claims, 8 Drawing Figures

ULTRASONIC IMAGING METHOD AND APPARATUS WITH ELECTRONIC BEAM FOCUSING AND SCANNING

ORIGIN OF THE INVENTION

The Government has rights in this invention pursuant to Contract No. 1-CB-74136.

BACKGROUND OF THE INVENTION

The use of a phased array transducer comprising a plurality of adjacent transducer elements for beam focusing is well known in the ultrasonic imaging art as shown, for example, in U.S. Pat. No. 3,936,791. The sequential operation of individual transducer elements or groups of elements for beam scanning also is well known as shown, for example, in U.S. Pat. No. 4,164,213. Also, focusing means which include a separate tapped delay line for each element of a transducer array are shown in U.S. Pat. No. 4,116,229. The taps are changed for dynamically focusing from minimum to maximum range the beam. Switching of the taps occurs during the signal reception period for generation of switching transients which are potentially deleterious. Also, a large number of relatively expensive tapped delay lines are required for the beam focusing and scanning operations provided by such prior art arrangement.

SUMMARY OF THE INVENTION AND OBJECTS

An object of this invention is the provision of an improved pulsed ultrasonic imaging system and method using electronic beam focusing, scanning, and received signal processing means by means of which a high resolution real-time image of a section of the interior of an object is obtained.

An object of this invention is the provision of a pulsed ultrasonic imaging system of the forementioned type wherein a relatively small number of fixed delay means are required for beam focusing and scanning of the section to be imaged.

An object of this invention is the provision of a pulsed ultrasonic B-scan method and apparatus by means of which a well-focused real-time image of the entire section to be imaged is obtained using simplified electronic focusing and scanning means.

Briefly, the above and other objects and advantages of this invention are achieved by recurrent transmission of ultrasonic energy pulses into the object. An ultrasonic transducer array comprising a plurality of adjacent transducer elements converts echo signals received from discontinuities within the object to equivalent electrical signals. A range gated signal processing means is responsive to electrical signals from transducer array elements produced by reflected ultrasonic waves received from within any one of a plurality of contiguous range zones within the section of the object to be imaged. The received signal processor includes beam focusing and scanning means for focusing transducer array elements at the range zone at which the processor is range gated and for scanning the zones. The resultant image line segment signals are supplied to a cathode ray tube for visual display of the entire imaged section. A digital scan converter may be used for temporary storage of the line segment signals, from which converter entire video line signals may be obtained for display at a TV monitor.

The nature of the invention, together with other objects, features and advantages thereof will be more fully understood from a consideration of the following detailed description of certain embodiments thereof taken in connection with the accompanying drawings.

BRIEF DESCRIPTION OF THE DRAWINGS

In the drawings, wherein like reference characters refer to the same parts in the several views.

DETAILED DESCRIPTION

Figure 1:
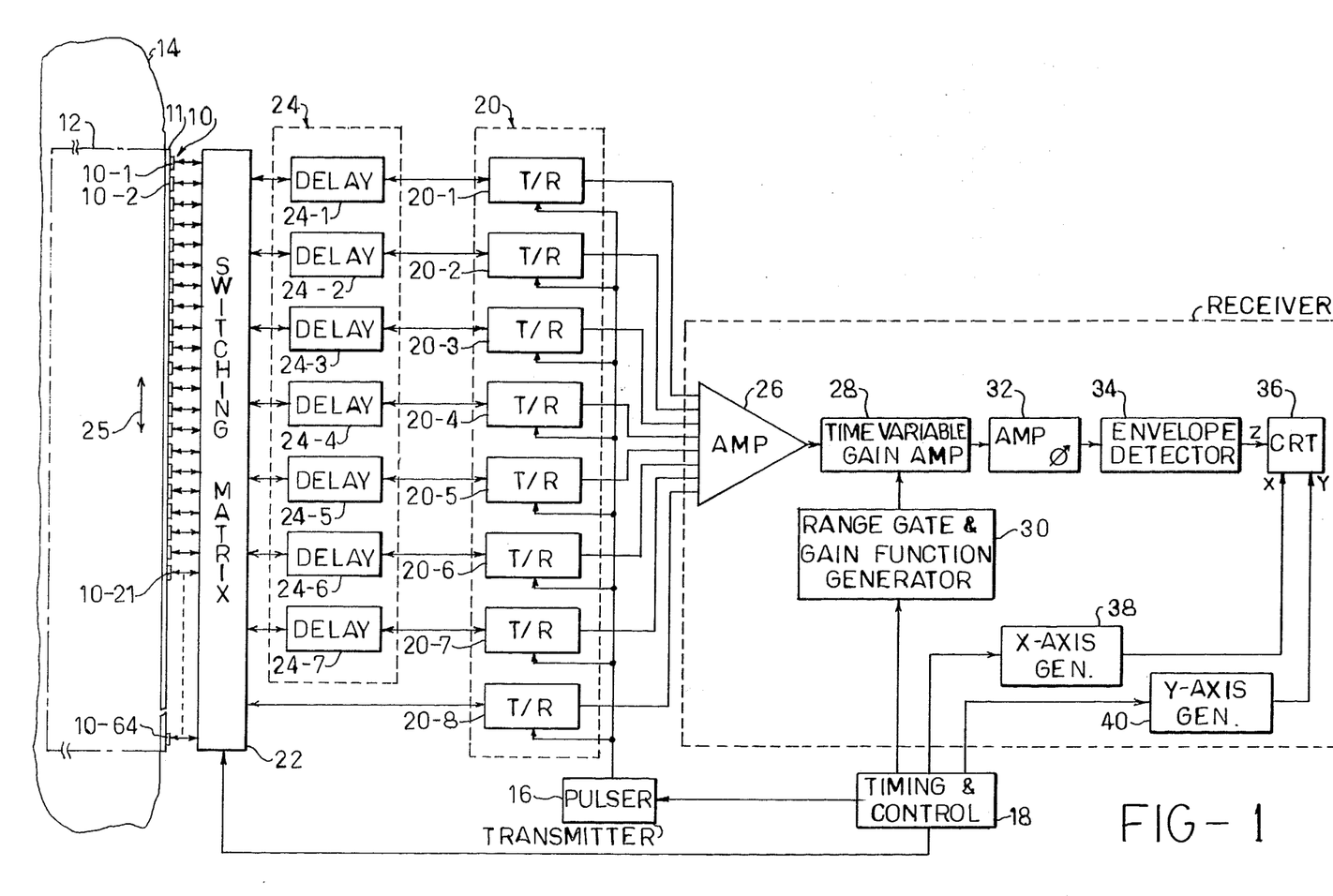
FIG. 1 is a block diagram showing an ultrasonic imaging system embodying the present invention.

Reference now is made to FIG. 1 wherein there is shown one embodiment of the novel ultrasonic imaging apparatus of the present invention comprising a linear transducer array 10 which, for purposes of illustration, includes 64 adjacent transducer elements 10-1 through 10-64. Preferably, the array is provided with a cylindrical lens focusing means 11 (see FIG. 2) for beam focusing in a plane normal to the plane of the section 12 within the object 14 to be imaged. With the illustrated arrangement, the section 12 lies in the longitudinal plane of the transducer array 10. The use of a cylindrical lens for such beam focusing is well known and requires no further description.

The transducer array 10 is included in a pulsed ultrasonic B-scan imaging system which also includes a transmitter comprising a pulser 16 which is supplied with recurrent timing pulses from a timing and control unit 18 for on-off control thereof. With the pulser turned on, a high frequency energy pulse is generated which is connected through transmit-receive switch unit 20 to a switching matrix 22. Time delay means 24, here comprising seven fixed signal delay elements 24-1 through 24-7, are included in the connection of seven of the transmit-receive switches 20-1 through 20-7, respectively, to the switching matrix 22. One transmit-receive switch 20-8 is directly connected to the switch matrix with no time delay means included in the interconnection thereof.

The transducer elements 10-1 through 10-64 of the transducer array are connected to the switching matrix 22 for connecting sets of different numbers thereof to the pulser 16. Timing and control signals from timing and control unit 18 are supplied to the switching matrix 22 for selecting a transducer element, or group of adjacent elements, to be activated during pulse transmitting and receiving operations. The signal delay means 24, for the delay of transmitter signals supplied to the transducer array, and of signals received from the array, provide for focusing of the beam at different depths within the section 12 of the object 14, the depth at which the array is focused being dependent upon the delay elements 24-1 through 24-7 employed in the connection of transducer elements to the pulsed B-scan transmitter/receiver. The axis of the beam is shifted along the transducer array 10 to a position dependent upon the transducer element, or set of adjacent elements, employed during transmitting and receiving operations. The functioning of the fixed delay means 24 for beam focusing at different depth zones within the section 12 to be imaged is described in greater detail hereinbelow in the description of the receiving operation. For present purposes, it will be understood that when the pulse transmitter 16 is turned on, a transducer element, or set of adjacent transducer elements, is energized for pulse generation of ultrasonic waves which are focused at one of a plurality of contiguous range zones within the section 12 to be imaged. The transducer element, or set of elements, which is activated is shifted along the array, in the direction of double-headed arrow 25, for scaning each of the range zones.

Reflected ultrasonic waves from discontinuities within the pulse-insonified object 14 are received by the transducer array 10 and converted to equivalent electrical signals by the individual transducer elements thereof. The output from one or more of the transducer elements 10-1 through 10-64 is connected through the transmit-receive switch means 20 to a summing amplifier 26. The transmit-receive switches 20-1 through 20-8 simply function to isolate transmitted signal pulses from the inputs to the summing amplifier. Obviously, preamplifiers, not shown, may be included in the connections of the transmit-receive switches to the summing amplifier 26 for pre-amplification of relatively low level signals from the transducer elements.

If desired, operation of the system may be such that no switching of the switching matrix 22 occurs between a pulse transmission and associated pulse receiving operation, in which case it will be apparent that beam focusing and positioning is the same during a single transmit-receive cycle of operation. Of, course, different sets of delay elements may be used during the transmitting and associated receiving operations, if desired. Sidelobe suppression, for example, may be enhanced by using slightly different focal patterns in transmission and reception. For simplicity, however, operation using the same beam pattern during a transmitting, receiving cycle of operation is described.

With the present system, the output from one or more transducer elements is connected to the input to the summing amplifier 26, during receiving operation. The output from the summing amplifier, which is related to a sum of the inputs, is supplied to a time variable gain amplifier 28 having a gain characteristic which varies as a function of time to compensate for loss of signal amplitude as it traverses the tissue of the subject 14. In the illustrated arrangement the gain of the amplifier 28 is varied in accordance with the output from range gate and gain function generator 30. The range gate and gain function generator 30 simply may comprise a ramp generator with an output signal which functions to increase the gain of the amplifier 28 in proportion to range to offset the loss of signal caused by acoustic absorption within the subject. Start-stop operation of the generator 30 is controlled by an output from the timing and control unit 18. The range gate and gain function generator output when turned off, before being triggered on, is such as to disable operation of the amplifier 28, for receiver range gating. With the illustrated arrangement, range gate operation of the receiver at four contiguous range zones within the subject is provided, in the manner described below. Obviously, range gating of the received signal at other locations in the system is possible, the invention not being limited to any particular gating means including the illustrated combination range gate and gain function generator 30.

The range gated signal from the time variable gain amplifier 28 is amplified by a variable gain amplifier 32, and the amplified output is detected by envelope detector 34 comprising, for example, a full wave rectifier followed by a low pass filter. The detector 34 output, which is related to the envelope of the broad band high frequency signal from the amplifier 32, is shown supplied to an ultrasonic image display device 36 comprising a cathode ray tube. Generally, a compression amplifier, not shown, is included in the connection of the detector output signal to the cathode ray tube 36 for matching the detected signal with characteristics of the cathode ray tube for proper display of the entire signal range. The detector output is applied as an input to the control grid of the cathode ray tube for intensity, Z-axis, control of the electron beam thereof.

For the illustrated B-scan display, cathode ray tube beam deflection in the X or horizontal, direction is proportional to the position of the ultrasonic beam across the array scanning path. An X-axis generator 38, triggered by synchronizing and control signals from the timing and control unit 18 provides a step function signal output which is supplied to the horizontal deflection system of the cathode ray tube 36 for shifting the trace on the cathode ray tube in accordance with the position of the ultrasonic beam axis of the transducer array 10.

Vertical, or Y-axis, deflection of the cathode ray tube is provided by a ramp generator 40 which is triggered by an output from the timing and control unit 18 at a selected time period following transmitter operation. The ramp generator 40 output is supplied to the vertical deflection system of the cathode ray tube 36 for vertical scanning of the trace. As mentioned above, a plurality of contiguous range zones are employed such that a plurality of individual signal trace segments are required for production of a complete video scanning line. In the illustrated arrangement, four such range zones are employed. As will become apparent, a complete high resolution B-scan ultrasonic image of the body part lying within the section 12 of the body part is provided at the face of the cathode ray tube 36 by display of the plurality of video line segments obtained from each of the range zones within the section 12.

Figure 2:
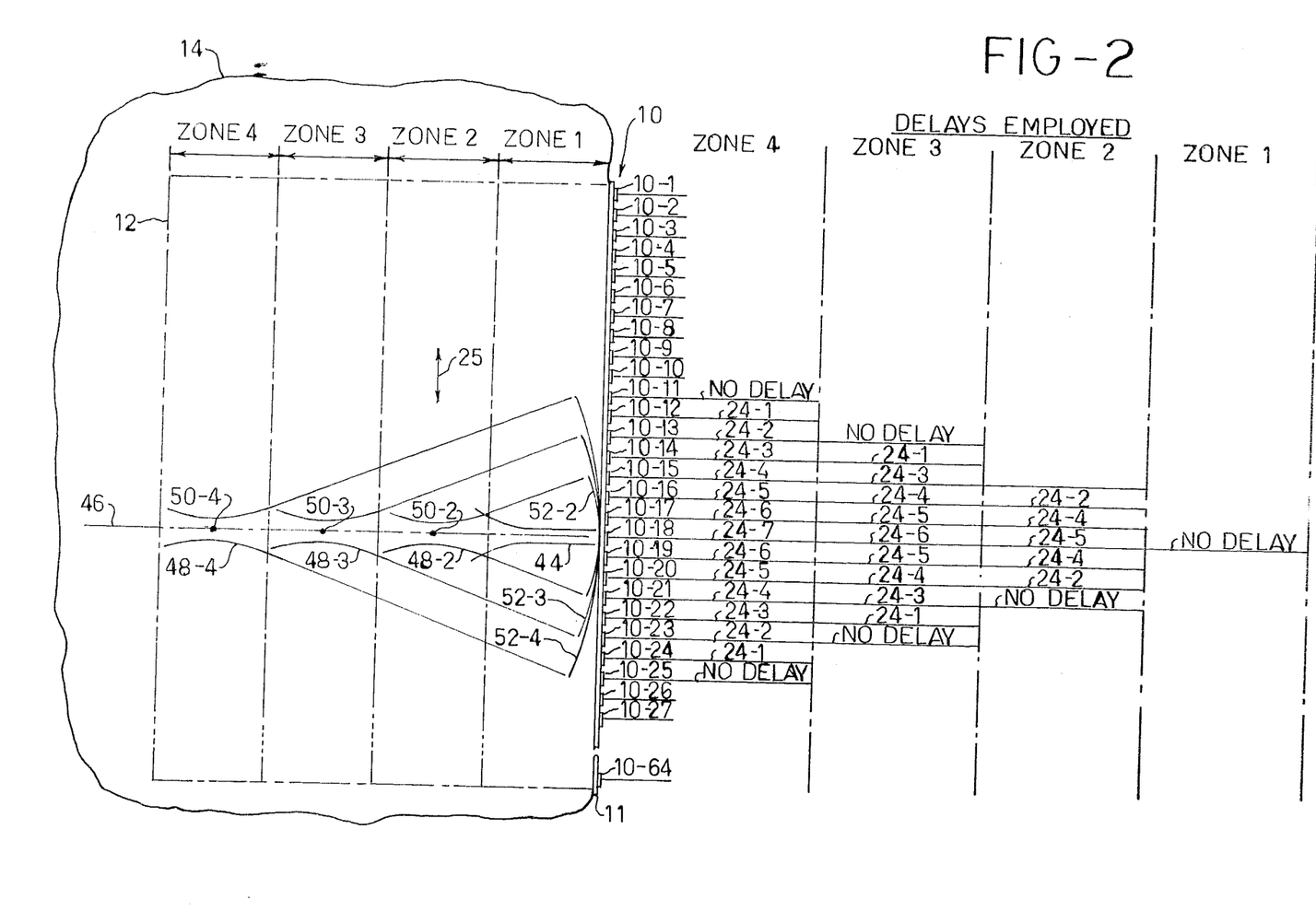
FIG. 2 is a diagram showing beam focusing of the transducer array at different range zones and time delay means associated with each zone.

In FIG. 2, to which reference now is made, the transducer array 10 and attached cylindrical lens 11 are shown in contact with the object 14, such as soft tissue of a body. The section 12 to be imaged is shown divided into a plurality of range zones and, for purposes of illustration, four range zones identified as zone 1 through zone 4 are depicted. The zones may be of equal or unequal width (i.e. range) as desired, with the number of range zones employed depending, among other things, upon desired resolution through the entire range of operation. As described above, the signal delay unit 24 comprises a set of seven delay means 24-1 through 24-7 and, during operation, sets of individual delay means, here ranging in number from zero to seven, are employed for focusing at the different range zones. For operation in zone 1, the switching matrix 22 simply functions to connect a selected one of the sixty-four transducer elements directly to the summing amplifier 26 through transmit-receive switch 20-8 without passage of the signal through any of the delay elements. The diagram of FIG. 2, under the heading "DELAYS EMPLOYED" indicates that no delay is employed for ZONE 1 operation. In FIG. 2, one line is shown leading from a single transducer element, here element 10-18, to the ZONE 1 section of the diagram to illustrate the fact that for operation at ZONE 1 the transducer elements are operated singly (in sets of one). It further will be understood that during ZONE 1 operation the receiver is range gated for processing signals received from the operative transducer element only during the time reflected signals are received from within the zone.

In range zone 1, immediately adjacent the transducer array, best resolution is obtained using single transducer elements. In the course of a complete scanning cycle, during which the entire section 12 is scanned, every transducer element of the array will have been individually operated to provide a line segment information signal for each transducer element in ZONE 1. In the FIG. 1 arrangement, the line segment signals are supplied to the cathode ray tube 36 as they are produced for real-time imaging thereat. With sixty-four transducer elements in the array, a total of sixty-four line segments per zone are obtained using the illustrated apparatus in the above described manner. In FIG. 2, the beam directional pattern for ZONE 1 operation, provided by activation of a single transducer element, is identified by reference numeral 44, and the beam axis during activation of said transducer element, here element 10-18 is identified by reference numeral 46.

Figure 3:
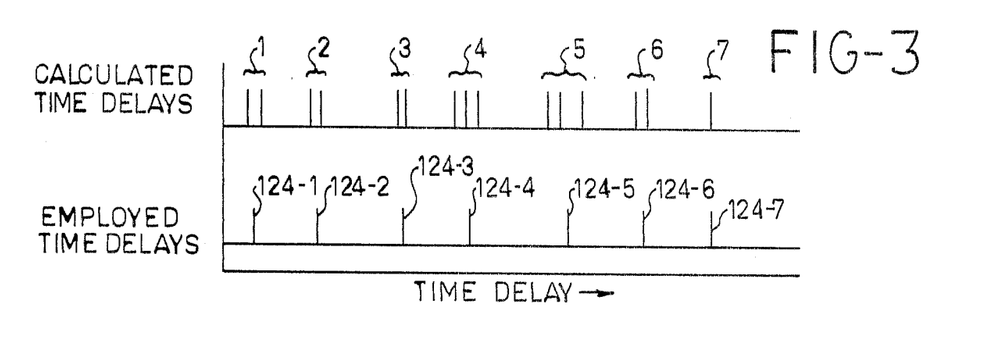
FIG. 3 is a graph showing the distribution of time delays required for focusing at the different range zones.

Signal delay elements included in signal delay unit 24 are employed for electronic beam focusing within range zones 2, 3 and 4. For operation in ZONE 4, for example, which zone is farthest from the transducer array 10, sets of fifteen transducer elements are employed, together with all seven of the delay means 24-1 through 24-7. The time delays provided by elements 24-1 through 24-7 increase as the reference numeral suffix increases; with a minimum time delay being provided by delay means 24-1 and a maximum time delay being provided by delay means 24-7. In FIG. 3, a plot of the time delays employed for the delay means 24-1 through 24-7 is shown.

For beam focusing at range ZONE 4, shown in FIG. 2, the outer-most transducer elements employed for focusing along beam axis 46, here transducer elements 10-11 and 10-25, are directly connected by the switching matrix 22 to the transmit-receive switch 20-8 without delay. Transducer element 10-18 at the beam axis 46 is connected by the switching matrix to the delay means 24-7 for maximum delay of transmitted and received signals. As is well understood, beam focusing is provided by use of progressively larger time delays in going from the outer most transducer elements to the center transducer element of the set employed. In FIG. 2, wherein the set of transducer elements 10-11 through 10-25 is used for focusing at ZONE 4 along beam axis 46, transducer elements 10-17 and 10-19 are connected through time delay element 24-6 to the summing amplifier 26. Similarly, other pairs of transducer elements, including elements 10-16 and 10-20, elements 10-15 and 10-21, elements 10-14 and 10-22, elements 10-13 and 10-23 and elements 10-12 and 10-24 are connected through time delay elements 24-5, 24-4, 24-3, 24-2 and 24-1, respectively, to the input of summing amplifier 26. During operation, different sets of fifteen transducer elements are connected by the switching matrix 22 for scanning range ZONE 4 while focusing thereat. Asjacent opposite ends of the transducer array the beam is formed using fewer transducer elements with a corresponding degradation in imaging thereat. With the illustrated arrangement, for each range zone, including range ZONE 4, sixty-four range gated line segment signals are obtained, which signals are processed by the receiver for display at the cathode ray tube 36. In FIG. 2 focused ultrasonic beams 48-2, 48-3 and 48-4 for focusing at points 50-2, 50-3 and 50-4 at range zones 2, 3 and 4, respectively, along beam axis 46, are shown, together with associated wave-fronts 52-2, 52-3 and 52-4.

From an examination of FIG. 2, it will be seen that a set of fewer transducer elements, and associated delay elements are used for operation at range zone 3 than range zone 4. Similarly, the set of transducer elements for focusing at range zone 2 includes fewer transducer elements and associated delays than the set for operation at range zone 3. In the illustrated arrangement, operation at range zones 3 and 2 include the use of 11 and 7 transducer elements, and 5 and 3 delay means, respectively. It will be seen, then, that at least some of the delay means 24-1 through 24-7 are employed for focusing at a plurality of different range zones. In the particular arrangement, delay means 24-1 is used for focusing at zones 3 and 4, delay means 24-2 is used for focusing at zones 2 and 4, delay means 24-3 is used for focusing at zones 3 and 4, delay means 24-4 is used for focusing at zones 2, 3 and 4, delay means 24-5 is used for focusing at zones 2, 3 and 4, and delay means 24-6 is used for focusing at zones 3 and 4.

Once the number of transducer elements to be included in each set thereof for operation at the different zones is determined, in a manner explained below, the delays required for focusing at the various focal points 50-2, 50-3, 50-4 within the respective range zones may be calculated. In FIG. 3, to which reference again is made, a plot of the calculated delay times for focusing at focal points 50-2, 50-3 and 50-4 is shown. From the plot it will be seen that the delay times are grouped along the time delay axis. Knowing the desired accuracy at the frequency of the highest expected return, the required accuracy of the time delays employed may be determined. For example only, for 0.1 wavelength accuracy at a frequency of about 15 MHz, time delays within an accuracy of approximately ±6.7 n sec are required. Consequently, any group of delay times falling within a range of 13.4 n sec may be satisfied by use of a single delay means. Obviously, the possible grouping will depend upon physical dimensions of the array in addition to the operating frequency and accuracy desired. In FIG. 3, seven sets of time delays, including one set of one delay provide the necessary delays for focusing at all four range zones.

Figure 4:
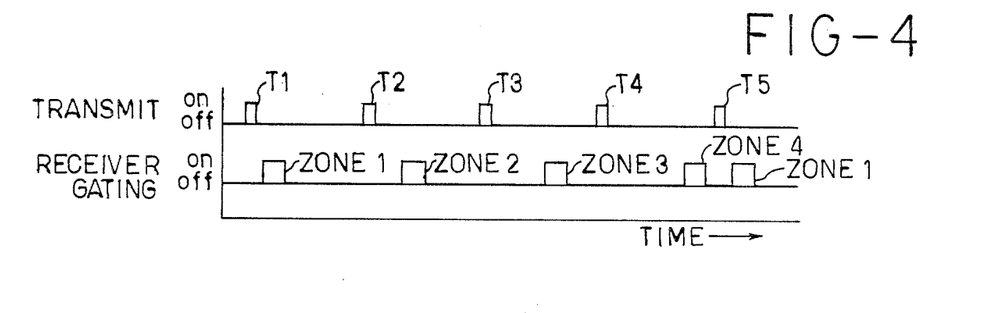
FIG. 4 is a timing diagram showing range gating of the receiver signal processor for operation at the different range zones.

With the illustrated invention, a single scan line segment is obtained from one of the four range zones for each transmit-receive cycle of operation. One sequence of transmitter and receiver gating operation which may be followed in scanning the image is shown in the timing diagram of FIG. 4 to which figure reference now is made. There, recurrent transmitter pulses T1, T2, T3, T4 and T5 are shown followed, in time, by range gating of the receiver for operation at range zones 1, 2, 3, 4 and 1, respectively. When the system employs four range zones, and sixty-four scan line segments are obtained for each zone, a total of 256 scan line segments are obtained, and displayed in the course of a complete scanning cycle.

Figures 5A, 5B:
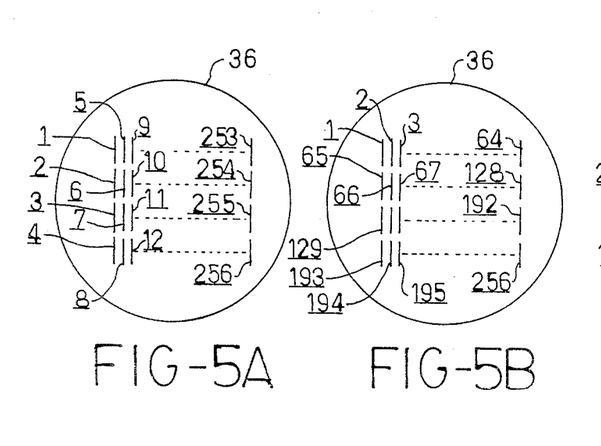
FIG. 5A, 5B and 5C diagrammatically show the spatial format of three different video frames obtained using three different zone scanning sequences.

It will be understood that the invention is not limited to any particular scanning sequence. This may be illustrated by reference to FIGS. 5A, 5B and 5C of the drawing showing three different scanning orders out of a substantially infinite number of possible sequences. In the drawings, the four line segments forming a single line are shown with gaps therebetween for ease in identifying the same. In practice, no such gaps exist, and the segments forming one line are contiguous. The order in which the line segments are obtained, and displayed, are identified by underlined numbers 1 through 256, only some of which are illustrated. In FIG. 5A it will be seen that all four line segments of a single line are consecutively obtained and displayed before stepping the beam axis to an adjacent position. For this operation, receiver range gating operation of the type illustrated in FIG. 4 would be employed.

In the FIG. 5B scanning sequence, an entire range zone is beam scanned, before range gating to an adjacent range zone. In the illustrated pattern, the range zone 1, 2, 3 and 4 are sequentially scanned.

Figure 5C:
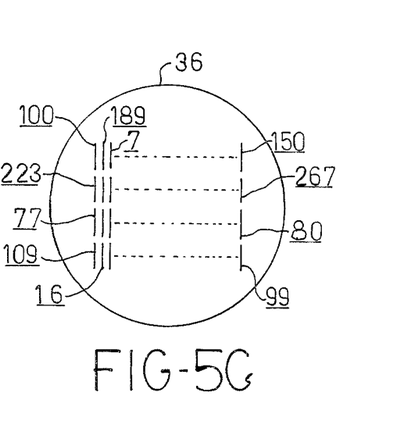

If desired, a substantially random scanning order may be employed such as illustrated in FIG. 5C. After all 256 line segments are obtained and displayed, the sequence is repeated. With any sequence of operation it is a simple matter to synchronize display of the line segment with the receiver gating and beam position.

The number of transducer elements to be included in each set thereof for focusing at the different range zones may be determined by calculating resolution within each range zone using different numbers of adjacent transducer elements in the set. The set which provides the best lateral resolution for the depth of the zone would then be used. In the illustrated arrangement only sets which include an odd number of transducer elements are employed such that the beam axis extends from the center of a transducer element. Obviously, a system using an even number of transducer elements may be used wherein the beam axis extends from a point between adjacent transducer elements. Also, by using both odd and even numbers of transducers in the sets thereof the number of lines obtainable is substantially doubled, without an increase in the number of transducer elements included in the array.

Figure 6:
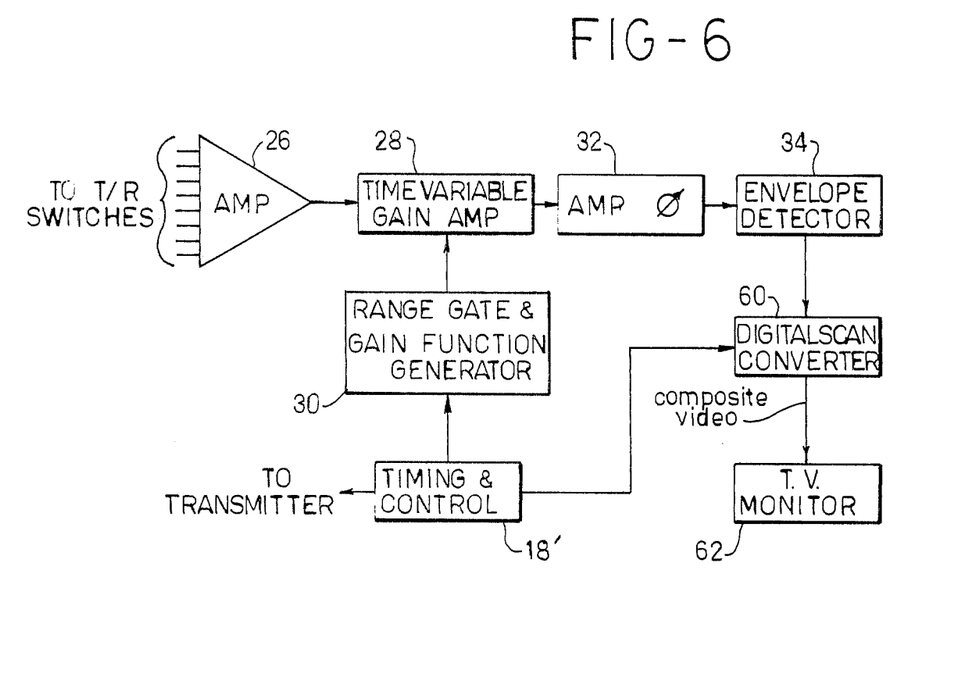
FIG. 6 is a block diagram similar to that of FIG. 1 but showing a portion of a modified form of this invention employing a digital scan converter.

The invention having been described in detail in accordance with requirements of the Patent Statutes, various other changes and modifications will suggest themselves to those skilled in this art. For example, it will be apparent that the display at the face of the cathode ray tube 36 may be converted by scan converter means responsive to such display to signals which may be employed by a conventional television type monitor or display. In another modification of the invention shown in FIG. 6, the electrical line segment signals from the envelope detector 34 are supplied to a digital scan converter 60 for conversion to a composite video signal which may be displayed at a conventional television monitor 62. Digital scan converters for such use are well known and often include a gray scale generator for generation of multibit digital signals which are temporarily stored in a read-write memory. Timing signals from timing and control means 18' also are supplied to the digital scan converter for control thereof. Complete video lines are read out of the digital scan converter for display at the monitor 62. Since sixty-four lines of video information are provided using the sixty-four element array, each line may be replicated eight times, if desired, to produce a 512 line display. Also, instead of simple replication, the signals for each synthetically generated scan line may be interpolated by appropriate mixing of signals from two adjacent actual scan lines. Such details of signal processing for furnishing a more pleasing presentation are well known and form no part of the present invention. It will be understood, however, that temporary storage of line segment signals required for digital scan conversion does not preclude real-time imaging by the system.

Other changes, as mentioned above, include the use of different delay means for associated transmitting and receiving operations for different beam focusing action. Also, it will be apparent that the invention is not limited to the use of four range zones. A system and method embodying the present invention employing eight range zones has been built and tested. Additionally the system may employ range zones of different size, if desired, with the size of each zone being dependent upon the desired resolution throughout the full depth of the section to be image. It is intended that the above and other such changes and modifications shall fall within the spirit and scope of the invention defined in the appended claims.

We claim:

1. In pulsed ultrasonic imaging apparatus for imaging a section within an object, which apparatus includes a linear transducer array and pulse transmitter means for energizing transducer elements of the array for beaming ultrasonic energy pulses into the section,
   beam focusing means for focusing of the transducer array at different range zones within the section to be imaged,
   beam scanning means for scanning the section to be imaged,
   range gated signal processing means responsive to the output from the transducer array for processing signals received from the range zone at which the beam is focused, and
   means for control of said beam focusing and range gated signal processing means to provide line segment signals from each of the range zones for use in visual display of the section to be imaged, a line segment signal for a single range zone being obtained with each operation of the pulse transmitter means.

2. In pulsed ultrasonic imaging apparatus as defined in claim 1 wherein sets of different numbers of transducer elements are employed for operation at the different range zones.

3. In pulsed ultrasonic imaging apparatus as defined in claim 2 wherein the number of transducer elements included in the sets thereof increases with distance of the range zone from the transducer array.

4. In pulsed ultrasonic imaging apparatus as defined in claim 3 wherein the set of transducer elements for operation in the range zone adjacent the transducer array consists of one.

5. In pulsed ultrasonic imaging apparatus as defined in claim 1 wherein said beam focusing means includes a plurality of signal delay means having different delay times.

6. In pulsed ultrasonic imaging apparatus as defined in claim 5 wherein at least some of said signal delay means are employed for focusing at different range zones.

7. In pulsed ultrasonic imaging apparatus as defined in claim 6 wherein said signal delay means comprise fixed signal delay means.

8. In pulsed ultrasonic imaging apparatus as defined in claim 1 including visual display means responsive to line segment signals from the signal processing means for display of line segments obtained from said different range zones to provide a composite image of the section of the object to be imaged.

9. In pulsed ultrasonic imaging apparatus as defined in claim 8 wherein said visual display means comprises a cathode ray tube and said line segments are displayed thereat as line segment signals are received from said signal processing means.

10. In pulsed ultrasonic imaging apparatus as defined in claim 8 including scan conversion means for temporary storage of line segment signals and transmission of complete video lines to said visual display means.

11. In pulsed ultrasonic imaging apparatus as defined in claim 8 wherein the range zones are contiguous and the line segment signals obtained from the different range zones are contiguously displayed to provide a composite visual display of the section to be imaged.

12. In pulsed ultrasonic imaging apparatus as defined in claim 1 wherein said beam focusing means is operable for beam focusing of transmitted ultrasonic energy pulses during pulse transmission.

13. In pulsed ultrasonic imaging apparatus as defined in claim 1 wherein said beam focusing means is operable for beam focusing of the transducer array during reception of ultrasonic energy pulses.

14. In pulsed ultrasonic imaging apparatus as defined in claim 1 wherein said beam focusing means is operable for beam focusing of the array during both ultrasonic pulse transmission and reception.

15. In a pulsed ultrasonic imaging method for real-time imaging of a section of the interior of an object from reflections from discontinuities within the section of recurrent transmitted pulses of ultrasonic energy,
  receiving by means of a linear transducer array comprising a plurality of adjacent transducer elements reflected wave pulses and converting the same to electrical signals,
  range gating electrical signals from the transducer array to obtain signals of a line segment from any one of a plurality of range zones within the section to be imaged,
  focusing said transducer array at the range zone at which the electrical signals are range gated, and
  scanning said section by scanning each of said range zones to obtain a plurality of separate line segment signals from each zone for use in imaging said section, said transducer array being focused at a single range zone for each pulse transmission of ultrasonic energy.

16. In a pulsed ultrasonic imaging method as defined in claim 15 including supplying said line segment signals from the plurality of range zones to a cathode ray tube for beam intensity modulation thereof for visual display of the line segments to provide a composite visual image of the section.

17. In a pulsed ultrasonic imaging method as defined in claim 16 including temporarily storing said line segment signals at a scan converter means prior to display thereof at the cathode ray tube.

18. In a pulsed ultrasonic imaging method as defined in claim 17 which includes supplying complete line signals comprising line segment signals from each range zone to the cathode ray tube from said scan converter means for display of the image.

19. In a pulsed ultrasonic imaging method as defined in claim 15 wherein said scanning is of the rectilinear B-scan type.

20. In a pulsed ultrasonic imaging method as defined in claim 15 wherein successive line segment signals are obtained from different range zones during scanning of the section.

21. In a pulsed ultrasonic imaging method as defined in claim 20 wherein the successive line segment signals from different range zones comprise a complete scan line for successively obtaining signals representative of complete scan lines.

22. In a pulsed ultrasonic imaging method as defined in claim 15 wherein complete range zones are successively scanned during scanning of the section.

23. In a pulsed ultrasonic imaging method as defined in claim 15 wherein the scanning of the section is performed non-sequentially.

24. In a pulsed ultrasonic imaging apparatus for use in imaging a section within an object, which apparatus includes a transducer array and pulse transmitting means for energizing transducer elements of the array for beaming ultrasonic energy pulses into the section,
  beam focusing means for focusing the transducer array at different range zones within the section to be imaged during an imaging process,
  beam scanning means for scanning the section to be imaged,
  range gated signal processing means responsive to the output from the transducer array for processing signals from a single range zone for each energy pulse beamed into the section,
  means for controlling both the beam focusing means and the range gated signal processing means to process signals from only the range zone at which transducer array is focused, and
  means responsive to range gated signals from the signal processing means obtained from a plurality of range zones for visual display of a composite image of the section.

25. In a pulsed ultrasonic imaging apparatus as defined in claim 24 wherein the transducer array is focused during pulse transmission by said beam focusing means.

26. In a pulsed ultrasonic imaging apparatus as defined in claim 24 wherein the transducer array is focused by said beam focusing means during the reception of ultrasonic energy pulses.

27. In a pulsed ultrasonic imaging apparatus as defined in claim 24 wherein the transducer array is focused by said beam focusing means during both pulse transmission and signal reception.

28. In a pulsed ultrasonic imaging apparatus as defined in claim 27 wherein the beam focusing means includes a plurality of fixed delay means together with means for connecting the pulse transmitting means and range gated signal processing means to elements of the transducer array through said fixed delay means.

REEXAMINATION CERTIFICATE (148th)
United States Patent [19]
Green et al.

[11] B1 4,305,296
[45] Certificate Issued Dec. 13, 1983

[54] ULTRASONIC IMAGING METHOD AND APPARATUS WITH ELECTRONIC BEAM FOCUSING AND SCANNING

[75] Inventors: Philip S. Green; Dilip G. Saraf, both of Atherton; James F. Havlice, Los Altos, all of Calif.

[73] Assignee: SRI International, Menlo Park, Calif.

Reexamination Request:
No. 90/000,350, Mar. 24, 1983

Reexamination Certificate for:
Patent No.: 4,305,296
Issued: Dec. 15, 1981
Appl. No.: 119,937
Filed: Feb. 8, 1980

[51] Int. Cl.³ .................................................. G01N 29/04
[52] U.S. Cl. .................................................. 73/626
[58] Field of Search .................... 73/626, 628, 633; 367/103, 138; 128/660

[56] References Cited

U.S. PATENT DOCUMENTS

| | | | |
|---|---|---|---|
| 3,936,791 | 2/1976 | Kossoff | 73/626 |
| 4,161,122 | 7/1959 | Buchner | 73/626 |
| 4,164,213 | 8/1979 | Hölzler | 73/626 |
| 4,241,610 | 12/1980 | Anderson | 73/626 |

OTHER PUBLICATIONS

Assenza et al., "Echographic Imaging with Dynamically Focused Insonification", *Ultrasonics*, Jan. 1980, pp. 38-42.

*Primary Examiner*—Anthony V. Ciarlante
*Attorney, Agent, or Firm*—Victor R. Beckman

[57] ABSTRACT

Method and apparatus for pulsed ultrasonic imaging of a section of the interior of an object from reflections by internal discontinuities of recurrent transmitted pulses of ultrasonic energy, are provided. There is included a transducer array comprising a plurality of adjacent transducer elements for converting echo signals received from discontinuities within the object to equivalent electrical signals. Range gated signal processing means are provided for processing electrical signals from the transducer array reflected from discontinuities within any one of a plurality of range zones within the section to be imaged to provided range gated signals representative of segments of lines within the section to be imaged. The signal processing means includes electronic receiver beam focusing and scanning means for focusing the transducer array at the range zone at which the signals are range gated and for scanning the same. Visual display means for visual display of the line segment signals are provided for visual display of the entire section to be imaged. The signal processing means may include digital scan converter means for temporary storage of received signals for display thereof at a conventional TV monitor. Different numbers of transducer elements are employed for beam forming at the different range zones; a maximum number of adjacent transducer elements being used for operation at the zone farthest from the transducer array, and decreasing numbers being used for zones nearer the array. The electronic beam focusing means includes a plurality of fixed delay means, at least some of which are employed for focusing at a plurality of range zones thereby minimizing the total number required for operation of the system.

REEXAMINATION CERTIFICATE ISSUED UNDER 35 U.S.C. 307.

ULTRASONIC IMAGING METHOD AND APPARATUS WITH ELECTRONIC BEAM FOCUSING AND SCANNING

NO AMENDMENTS HAVE BEEN MADE TO THE PATENT

AS A RESULT OF REEXAMINATION, IT HAS BEEN DETERMINED THAT:

The patentability of claims 1-28 is confirmed.

* * * * *

REEXAMINATION CERTIFICATE (1052nd)
United States Patent [19]
Green et al.

[11] B2 4,305,296
[45] Certificate Issued May 9, 1989

[54] ULTRASONIC IMAGING METHOD AND APPARATUS WITH ELECTRONIC BEAM FOCUSING AND SCANNING

[75] Inventors: Philip S. Green; Dilip G. Saraf, both of Atherton; James F. Havlice, Los Altos, all of Calif.

[73] Assignee: SRI International, Menlo Park, Calif.

Reexamination Request:
No. 90/001,500, Apr. 29, 1988

Reexamination Certificate for:
Patent No.: 4,305,296
Issued: Dec. 15, 1981
Appl. No.: 119,937
Filed: Feb. 8, 1980

Reexamination Certificate B1 4,305,296 issued Dec. 13, 1983.

[51] Int. Cl.⁴ ............................................. G01N 29/04
[52] U.S. Cl. ..................................................... 73/626
[58] Field of Search .......................... 73/626, 612, 614; 367/105; 128/661.01

[56] References Cited
U.S. PATENT DOCUMENTS

| | | | |
|---|---|---|---|
| 3,548,642 | 12/1970 | Flaherty et al. | 73/602 |
| 3,815,409 | 6/1974 | Macovski | 73/615 |
| 3,911,730 | 10/1975 | Niklas | 73/626 |
| 4,019,169 | 4/1977 | Takamizawa | 73/626 |
| 4,119,938 | 10/1978 | Alais | 73/626 |
| 4,180,790 | 12/1979 | Thomas | 73/626 |
| 4,235,111 | 11/1980 | Hassler | 73/626 |
| 4,241,608 | 12/1980 | Dees et al. | 73/606 |

FOREIGN PATENT DOCUMENTS

53-142071 12/1978 Japan .

941573 11/1963 United Kingdom .................. 73/626

*Primary Examiner*—John E. Chapman

[57] ABSTRACT

Method and apparatus for pulsed ultrasonic imaging of a section of the interior of an object from reflections by internal discontinuities of recurrent transmitted pulses of ultrasonic energy, are provided. There is included a transducer array comprising a plurality of adjacent transducer elements for converting echo signals received from discontinuities within the object to equivalent electrical signals. Range gated signal processing means are provided for processing electrical signals from the transducer array reflected from discontinuities within any one of a plurality of range zones within the section to be imaged to provided range gated signals representative of segments of lines within the section to be imaged. The signal processing means includes electronic receiver beam focusing and scanning means for focusing the transducer array at the range zone at which the signals are range gated and for scanning the same. Visual display means for visual display of the line segment signals are provided for visual display of the entire section to be imaged. The signal processing means may include digital scan converter means for temporary storage of received signals for display thereof at a conventional TV monitor. Different numbers of transducer elements are employed for beam forming at the different range zones; a maximum number of adjacent transducer elements being used for operation at the zone farthest from the transducer array, and decreasing numbers being used for zones nearer the array. The electronic beam focusing means includes a plurality of fixed delay means, at least some of which are employed for focusing at a plurality of range zones thereby minimizing the total number required for operation of the system.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 8, 12-14, and 25-27 are cancelled.

Claims 1, 5, 9-11, 15, 16, 24 and 28 are determined to be patentable as amended.

Claims 2-4, 6, 7, and 17-23, dependent on an amended claim, are determined to be patentable.

1. In a pulsed ultrasonic imaging apparatus for imaging a section within an object, which apparatus includes
   a linear transducer array, [and]
   pulse transmitter means for energizing transducer elements of the array for beaming ultrasonic energy pulses into the section,
   [beam] *electronic* focusing means for focusing of the transducer array at different *contiguous* range zones within the section to be imaged,
   beam scanning means for scanning the section to be imaged,
   range gated signal processing means responsive to the output from the transducer array for processing signals received from *only* the range zone at which the [beam] *transducer array* is focused, *said transducer array being focused by said focusing means at only one of said range zones during each pulse transmission and associated signal processing operation*, [and]
   means for control of said [beam] *electronic* focusing *means, beam scanning means,* and range gated signal processing means to provide line segment signals from each of the range zones for use in visual display of the section to be imaged, a line segment signal for a single range zone being obtained with each operation of the pulse transmitter means, and
   *visual display means responsive to line segment signals from each of the range zones for display of a composite image of said section.*

5. In pulsed ultrasonic imaging apparatus as defined in claim 1 wherein said [beam] *electronic* focusing means includes a plurality of signal delay means having different delay times.

9. In pulsed ultrasonic imaging apparatus as defined in claim [8] *1* wherein said visual display means comprises a cathode ray tube and said line segments are displayed thereat as line segment signals are received from said signal processing means.

10. In pulsed ultrasonic imaging apparatus as defined in claim [8] *1* including scan conversion means for temporary storage of line segment signals and transmission of complete video lines to said visual display means.

11. In pulsed ultrasonic imaging apparatus as defined in claim [8] *1* wherein [the range zones are contiguous and] the line segment signals obtained from the different range zones are contiguously displayed [to provide a composite visual display of the section to be imaged].

15. In a pulsed ultrasonic imaging method for realtime imaging of a *unitary* section of the interior of an object from reflections from discontinuities within the section of recurrent transmitted pulses of ultrasonic energy,
   *transmitting by means of a linear transducer array comprising a plurality of adjacent transducer elements recurrent pulses of ultrasonic energy into the interior of an object,*
   receiving by means of [a] *the* linear transducer array [comprising a plurality of adjacent transducer elements] reflected wave pulses and converting the same to electrical signals,
   range gating electrical signals from the transducer array to obtain signals of a line segment from any one of a plurality of *contiguous* range zones within the section to be imaged,
   *during both pulse transmission and reception, electronically* focusing the transducer array at the range zone at which the electrical signals are range gated, [and]
   scanning said section by scanning each of said range zones to obtain a plurality of separate line segment signals from each zone for use in imaging said section, said transducer array being focused at a single range zone for each pulse transmission *and associated reception* of ultrasonic energy , *and*
   *displaying a composite image of said unitary section using line segment signals from each of said range zones.*

16. In a pulsed ultrasonic imaging method as defined in claim 15 [including] *wherein said displaying step includes* supplying said line segment signals from the plurality of range zones to a cathode ray tube for beam intensity modulation thereof for visual display of the line segment signals to provide [a] *said* composite visual image of the *unitary* section.

24. In a pulsed ultrasonic imaging apparatus for use in imaging a *unitary* section within an object, which apparatus includes,
   a transducer array, [and]
   pulse transmitting means for energizing transducer elements of the array for beaming ultrasonic energy pulses into the section,
   [beam] *electronic* focusing means for focusing the transducer array at different *contiguous* range zones within the section to be imaged *during an imaging process, ultrasonic energy beamed into the section being focused at only one of said range zones by said electronic focusing means during pulse transmission operation,*
   [beam scanning means for scanning the section to be imaged,]
   range gated signal processing means responsive to the output from the transducer array for processing signals from a single range zone for each energy pulse beamed into the section, *said transducer being focused at said signal range zone during operation of said signal processing means,*
   means for controlling both the [beam] *electronic* focusing means and the range gated signal processing means to process signals from only the range zone at which *the* transducer array is focused *dur-*

*ing each pulse transmission and associated signal processing operation and obtain a line segment signal from the range zone at which the transducer array is focused.* [and]

*scanning means for scanning the section to be imaged to obtain a plurality of separate line segment signals from each of said range zones, and* means responsive to range gated signals from the signal processing means obtained from [a plurality of] *each of the different* range zones for visual display of a composite image of the *unitary* section.

28. In a pulsed ultrasonic imaging apparatus as defined in claim [27] *24* wherein the [beam] *electronic* focusing means includes a plurality of fixed delay means together with means for connecting the pulse transmitting means and range gated signal processing means to elements of the transducer array through said fixed delay means.

* * * * *